United States Patent [19]

Rattner

[11] Patent Number: 5,703,922
[45] Date of Patent: Dec. 30, 1997

[54] THERAPY APPARATUS WITH A RADIATION SOURCE

[75] Inventor: Manfred Rattner, Grossenseebach, Germany

[73] Assignee: Siemens Aktiengesellschaft, Munich, Germany

[21] Appl. No.: 660,444

[22] Filed: Jun. 7, 1996

[30] Foreign Application Priority Data

Jun. 7, 1995 [DE] Germany ............... 195 20 748.3

[51] Int. Cl.[6] .................................................. A61N 5/10
[52] U.S. Cl. ..................... 378/65; 128/653.1; 601/2; 378/208
[58] Field of Search ................... 5/600, 601; 128/653.1; 601/2, 4; 378/65, 208, 209, 193, 195, 196, 197, 198, 177, 178, 179

[56] References Cited

U.S. PATENT DOCUMENTS

| | | | |
|---|---|---|---|
| 3,942,531 | 3/1976 | Hoff et al. | 128/328 |
| 4,526,168 | 7/1985 | Hassler et al. | 128/328 |
| 4,749,177 | 6/1988 | Schäfer et al. | 269/323 |
| 5,044,354 | 9/1991 | Goldhorn et al. | 601/4 |
| 5,072,721 | 12/1991 | Weiler et al. | 601/4 |
| 5,285,772 | 2/1994 | Rattner | 128/24 |
| 5,545,124 | 8/1996 | Krause et al. | 601/2 |

FOREIGN PATENT DOCUMENTS

OS 29 42 193   4/1981   Germany .
G 81 00 04 8   8/1981   Germany .

OTHER PUBLICATIONS

ACTA Medicotechnica, vol. 1, 1980, p. 24.
Brochure for Philips Medizin System MFL 5000.

*Primary Examiner*—Don Wong
*Attorney, Agent, or Firm*—Hill, Steadman & Simpson

[57] ABSTRACT

A therapy apparatus has a radiation source and a base part standing on the floor of the treatment room, the radiation source being connected to the base part and the base part containing devices required for the operation of the radiation source. The base part has an upper part fashioned at least as part of a patient bearing assembly. At least one further part of the patient bearing assembly is attached to the base part, at least during operation of the therapy apparatus.

22 Claims, 6 Drawing Sheets

THERAPY APPARATUS WITH A RADIATION SOURCE

BACKGROUND OF THE INVENTION

1. Field of the Invention

The present invention is directed to a therapy apparatus of the type having a radiation source and with a base part standing on the floor of the treatment room, the radiation source being connected to the base part and said base part containing the devices required for the operation of the therapy apparatus.

Such a therapy apparatus can have, for example, a source of acoustic waves or a source of electromagnetic waves as the radiation source.

2. Description of the Prior Art

Normally, the base part of therapy apparatus of the above type is movable, so that the apparatus can be positioned relative to a patient seated on a bed, a chair or the like such that the radiation source is aligned to the region to be treated. The patient, however, must often assume an uncomfortable posture. Alleviation of this problem could be created by providing the therapy apparatus with a suitable patient bearing means; this, however, would lead to a structure of the therapy apparatus requiring a large amount.

Patient bearing means that have a base part standing on the floor with an upper part fashioned the patient supporting structure are disclosed by the German periodical *acta medicotechnica*, No.1/1980, German Utility Model 81 00 048, German OS 29 42 193 and European Application 02 41 701. The massive structure of these patient bearing means and the large space requirements associated therewith, however, make these unusable for use as a mobile diagnostic or system for therapy use.

The publication "Philips-Medizinsysteme MFL5000—der urologische Arbeitsplatz für die Diagnose und Therapie" also discloses a therapy means (lithotriptor) has a stationary base part, a separate patient bearing table attached thereto, a pivotable X-ray system and a pivotable shockwave applicator. The shockwave applicator, however, can only be pivoted in an extremely limited range in order to assure access to the kidney region. Other body regions cannot possibly be reached for therapy purposes without patient displacement except on the basis of swivel motions of the shockwave applicator.

The therapy apparatus disclosed by German OS 41 35 177 is in fact portable but is implemented without patient bearing means. Further, the therapy head of the therapy apparatus is only pivotable by 180°, and as a result the freedom of motion of the therapy head is limited and, like that of the therapy apparatus from the Philips publication, is likewise limited to simple swivel motions. An unrestricted alignment of the radiation source onto a body region of a patient is likewise not possible with this therapy apparatus without the patient having to accept discomfort.

SUMMARY OF THE INVENTION

An object of the present invention is to provide an apparatus of the type initially described wherein discomfort for the patient is alleviated and a compact structure of the therapy apparatus is nonetheless assured.

This object is inventively achieved by a therapy apparatus with a radiation source and a base part standing on the floor of the treatment room, the radiation source being connected to the base part and the base part containing devices required for the operation of the therapy apparatus, and that has an upper part fashioned at least as part of a patient bearing means. Without an additional space requirement, the inventive therapy apparatus is at least provided with the part of a patient bearing means in this way. The patient is thus placed on the upper part in a position relative to the radiation source that is defined at least within certain limits. With little outlay, it is therefore possible to attach the radiation source to the base part such that it can be aligned to the region of the patient to be treated required, without forcing the patient to assume an uncomfortable position.

Since the patient can normally assume only a sitting position on the upper part, in a version of the invention at least a further part of the patient bearing means is attached to the base part at least during operation of the therapy apparatus. More versatile bearing possibilities for the patient are obtained in this way, these being even more versatile when the further part of the patient bearing means is removably attached to the base part and can be attached to the base part at different locations. The further part of the patient bearing means can be directly attached to the base part, or can be indirectly attached to the base part via attachment to the upper part.

A further improvement of the bearing possibilities is achieved when the further part of the patient bearing means is adjustable relative to the upper part.

For achieving a targeted treatment, in another version of the invention that the source is adjustably attached to the base part. It can be attached to the base part with a column, an articulated arm or an articulated arm connected to a column.

According to a preferred embodiment of the invention, the radiation source is adjustable at least in such a range that arbitrary locations of the upper part torso of the apparatus can be reached. Dependent on the position assumed by the patient, it is thus assured that at least the body regions of the patient located on the upper part are accessible to the radiation source.

For achieving universal applicability of the therapy apparatus, the source thereof in one embodiment is adjustable in a range of adjustment such that a patient who is seated on a bearing means different from the bearing means of the therapy apparatus and located close to the therapy apparatus can also be reached. There is thus the also possibility of treating, for example, a patient lying in a bed.

In order to employ the therapy apparatus in portable fashion, the base part thereof is provided with wheels in one version of the invention. In order to be independent from the power mains, the base part contains an energy storage element, particularly an electrical accumulator whose capacity is adequate in order to store the energy for at least one therapy procedure.

In order to be able to utilize the therapy apparatus for the treatment of pain in the way disclosed in German OS DE 43 15 282, in a preferred embodiment of the invention a source of focussed acoustic waves, particularly a shockwave source, is provided as the radiation source.

Since it is expedient for an exact alignment of the radiation source to the region to be treated to be able to precisely locate this region, in an embodiment of the invention an ultrasound locating means is provided whose diagnostic ultrasound transducer is preferably recessed in the radiation source, so that a defined allocation of the ultrasound diagnostic transducer and the radiation source is assured in a simple way.

In order to be able to undertake examinations with the ultrasound locating means independently of the radiation source, or of the therapy apparatus, in a version of the invention the diagnostic ultrasound transducer of the ultrasound locating means can be removed from the radiation source.

In order to facilitate observation of the monitor of the ultrasound locating means for the attending personnel, in one embodiment a holder for the monitor is provided at the base part.

The upper part, moreover, closes the base part in the manner of a cover. If the upper part is made removable from the base part, good accessibility to the devices located in the inside of the base part and required for the operation of the therapy apparatus is established. Maintenance work can therefore be carried out with little outlay.

DESCRIPTION OF THE PREFERRED EMBODIMENTS

The invention is explained below with reference to the example of a therapy apparatus shown in the drawings that is provided for pain therapy and that has a acoustic shockwave source as the radiation source.

Figure 1:
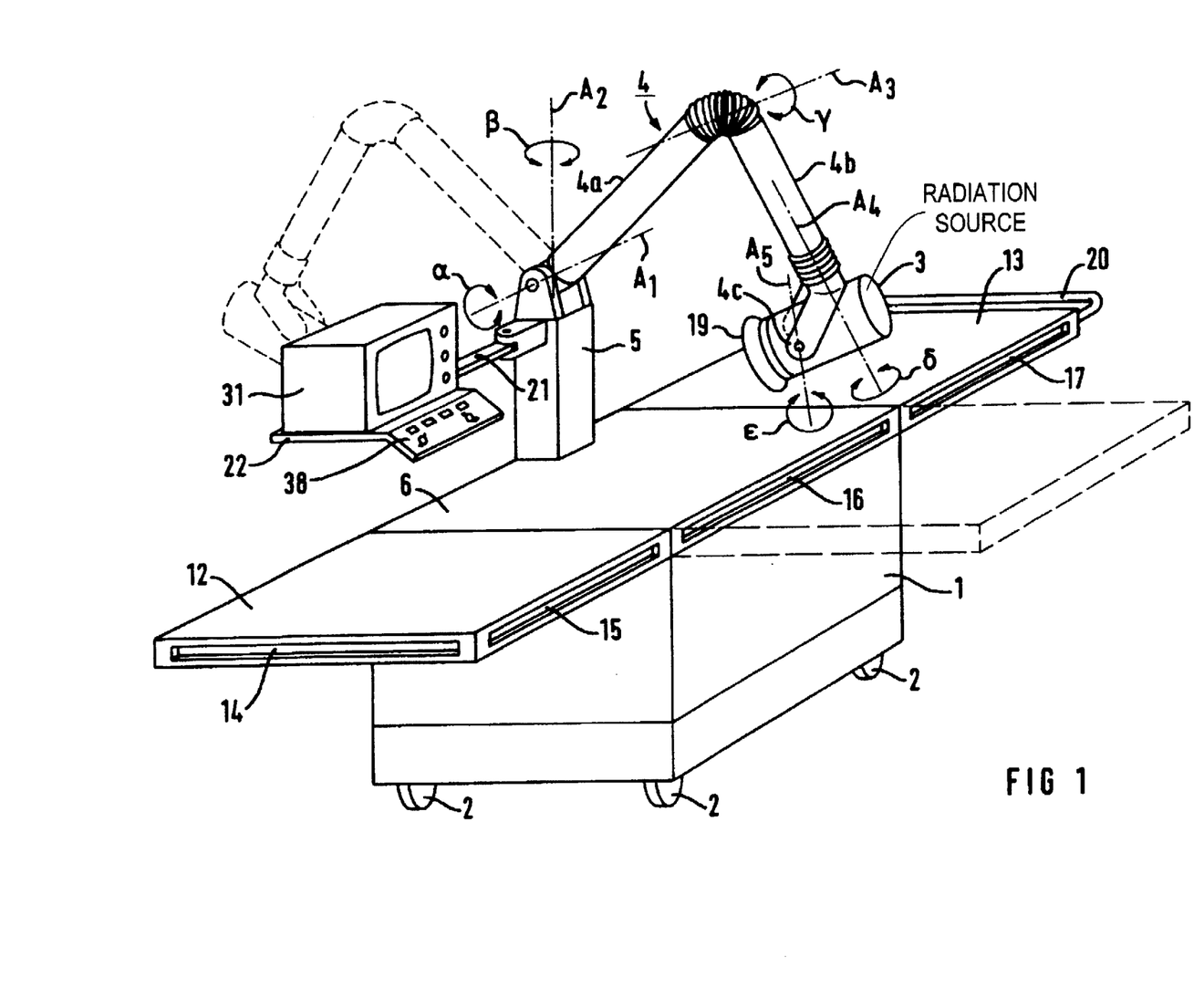
FIG. 1 is a perspective view of the inventive therapy apparatus.

According to FIG. 1, the inventive therapy apparatus has a base part 1 that stands on the floor of the treatment room with wheels 2 in order to assure the portability of therapy apparatus.

Figure 9:
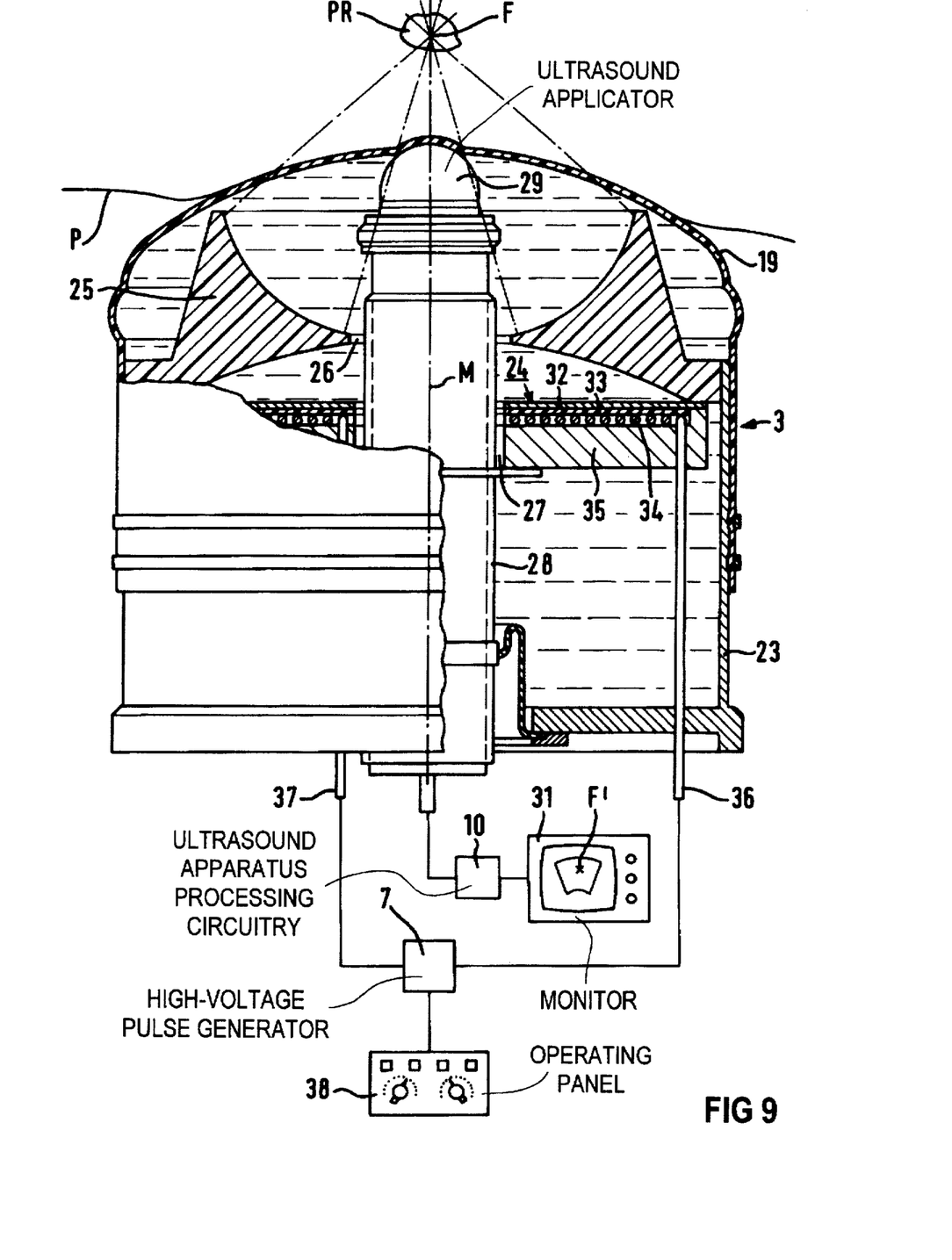
FIG. 9 is a schematic illustration of a longitudinal section through the radiation source of the therapy apparatus of FIGS. 1 through 8.

A shockwave source 3 shown in greater detail in FIG. 9, is provided as the radiation source, which generates focussed acoustic shockwaves and which is adjustably connected to the base part 1 via an articulated arm 4 and a column 5.

The adjustability of the shockwave source 3 is first assured by means of the articulated arm 4 being rotatably connected to the column 5, so as to be pivotable around a horizontal axis $A_1$ in the direction of the double arrow α and around a vertical axis $A_2$ in the direction of the double arrow β. Adjustability of the shockwave source 3 is also facilitated by the articulated arm 4 being composed of two arm parts $4a$ and $4b$ and a fork $4c$, the two arm parts $4a$ and $4b$ being connected to one another so as to be pivotable around a horizontal axis $A_3$ in the direction of the double arrow y. The fork $4c$ is rotatable in the direction of the double arrow δ at the arm part $4b$ around an axis A4 proceeding parallel to the longitudinal axis of the arm part $4b$. A further adjustment possibility is provided by the shockwave source 3 being accepted in the fork $4c$ so as to be pivotable around an axis $A_5$ in the direction of the double arrow ε.

The devices required for the operation of the therapy apparatus are located in the base part 1, which is closed by a removable upper part 6 in the manner of a cover. For example, the base part 1 can contain a high-voltage pulse generator 7 required for the operation of the shockwave source 3, an accumulator 8 permitting mains independent operation of the therapy apparatus for the duration of at least an average treatment procedure, a water supply 9 required for the operation of the shockwave source 3, and ultrasound apparatus processing circuitry 10 serving, together with an ultrasound application 29 (FIG. 9) and a monitor 31 (FIGS. 1 and 9), for locating the region to be treated. The lines leading to the shockwave source 3 are conducted through the column 5 and the articulated arm 4.

Figure 8:
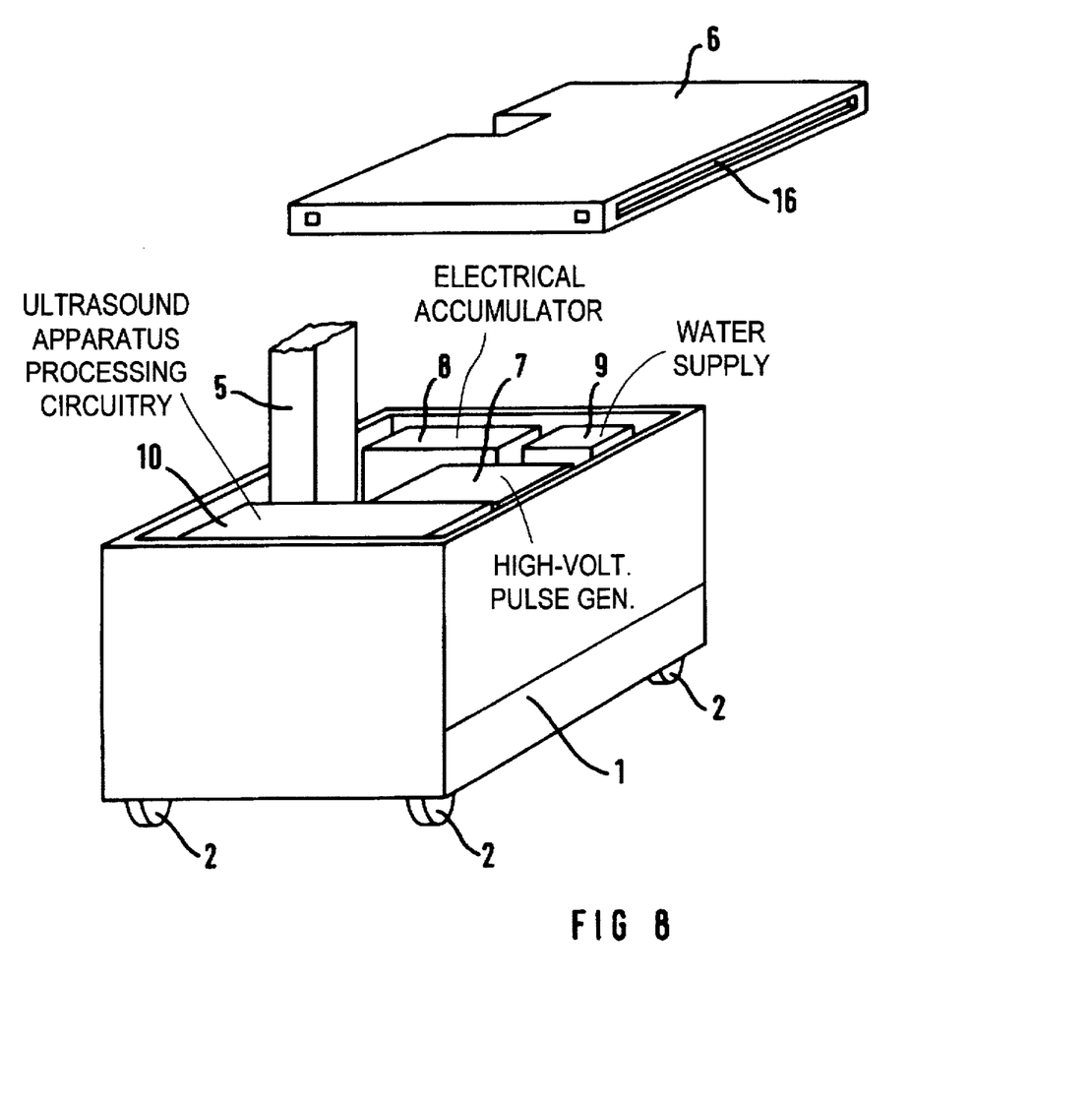
FIG. 8 is a perspective view of the inventive therapy apparatus with the upper part removed.

As FIG. 8 shows, the devices 7 through 10 required for the operation of the therapy apparatus are modular and are arranged for easily accessibly, so that the inventive therapy apparatus is maintenance-friendly.

The upper part 6 functions not only as a cover for the base part 1 but also constitutes a part of the patient bearing assembly of the inventive therapy apparatus. The patient bearing assembly in addition to the upper part 6, also includes the bearing plane sections 12 and 13. In a manner not shown in greater detail, these sections 12 and 13 are pivotably attached to the ends of the upper part 6 lying opposite one another so that they can assume different angles of inclination relative to the upper part 6, which is arranged in a horizontal plane, as can be seen from FIGS. 1 through 7. There is also the possibility of directly attaching the bearing plate sections 12 and 13 to the base part 1.

In this way, it is possible to individually adapt the patient bearing assembly of the inventive therapy apparatus to a large variety of treatment cases.

The adaptability of the patient bearing assembly is further enhanced by the bearing plate section 13 being removable from the upper part 6 so that it can be attached to that longitudinal edge of the upper part 6 lying opposite the column 5, as indicated with broken lines in FIG. 1. For example, there is then the possibility of seating a patient on his or her side with flexed legs.

Figure 2:
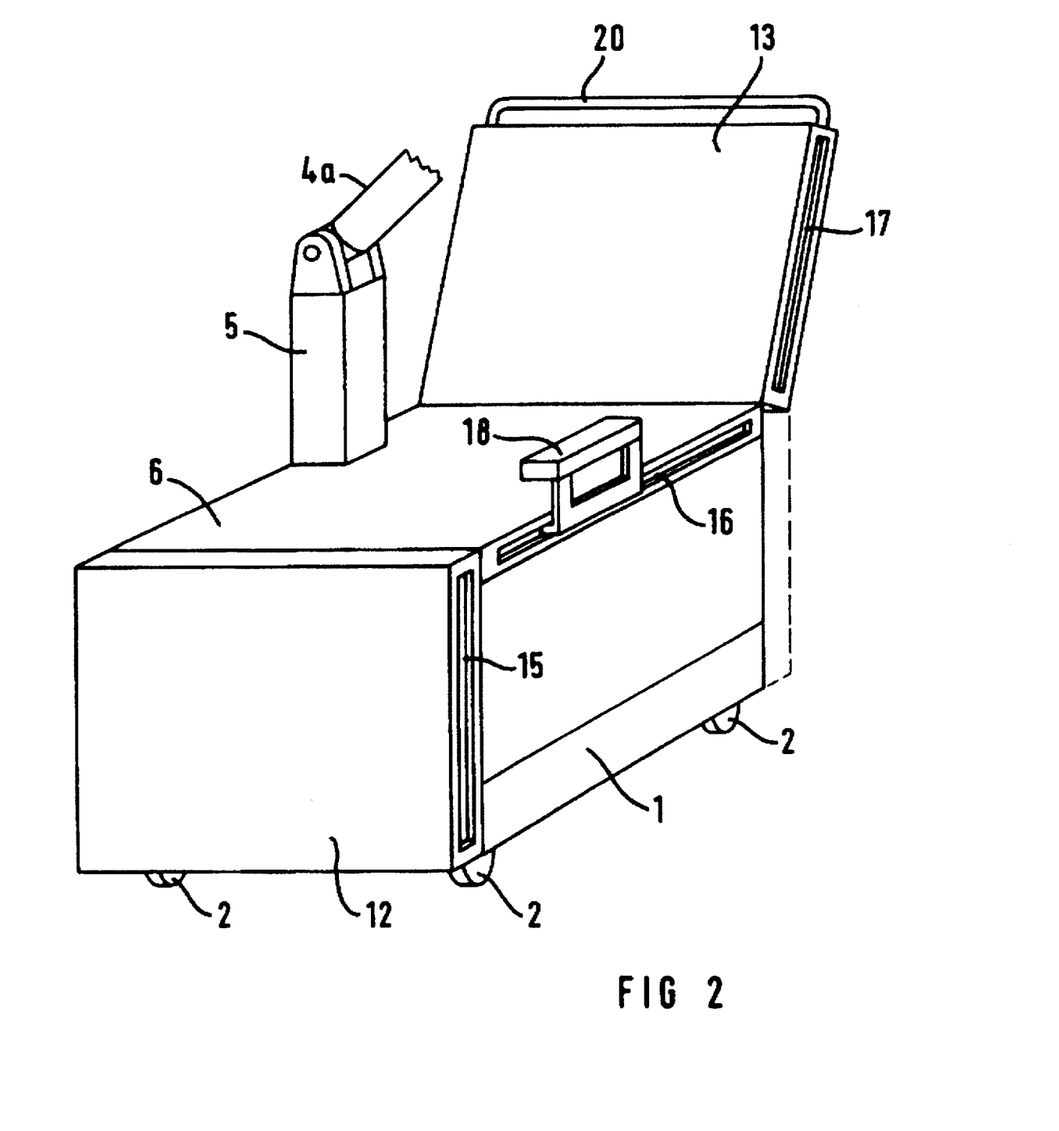
FIGS. 2–3 are respective perspective views of the therapy apparatus of FIG. 1 in other operating conditions.
Figure 3:
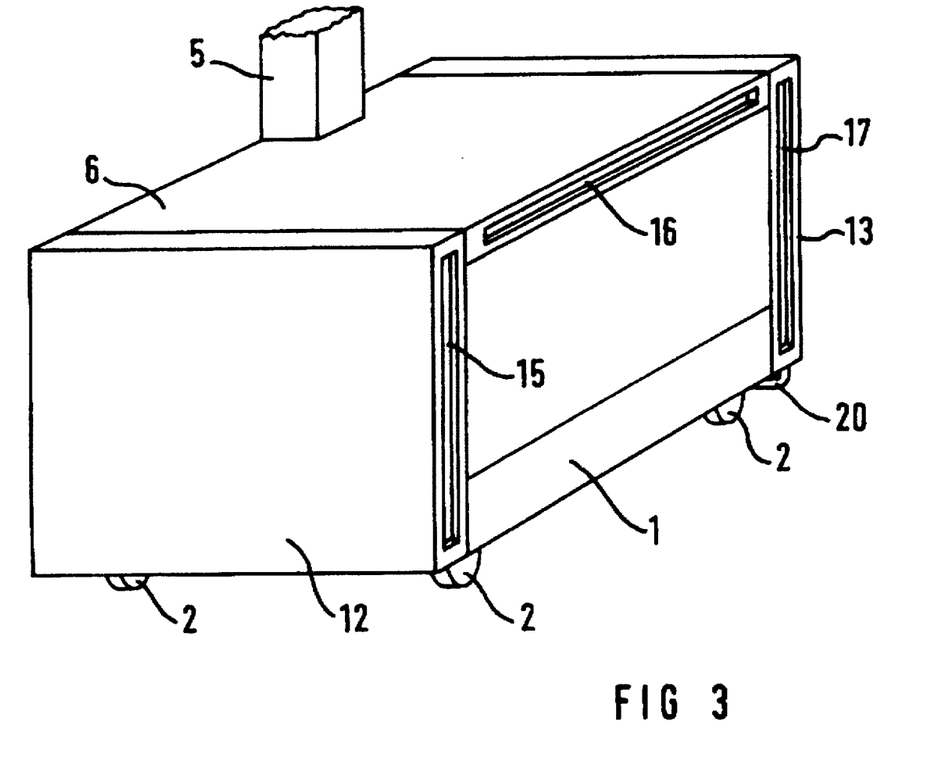
Figure 4:
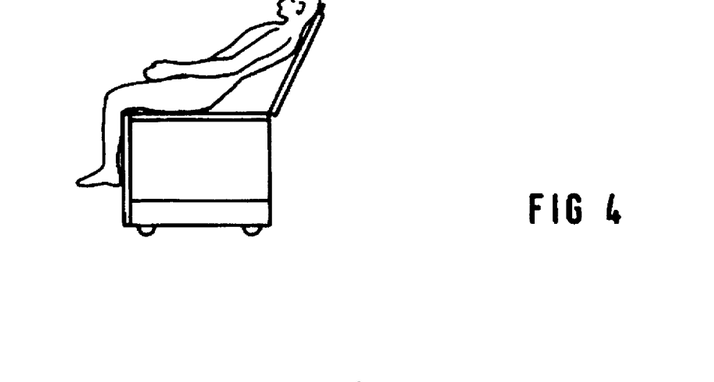
FIGS. 4–7 are respective schematic views of the therapy apparatus of FIGS. 1–3 in various operating conditions.
Figure 5:
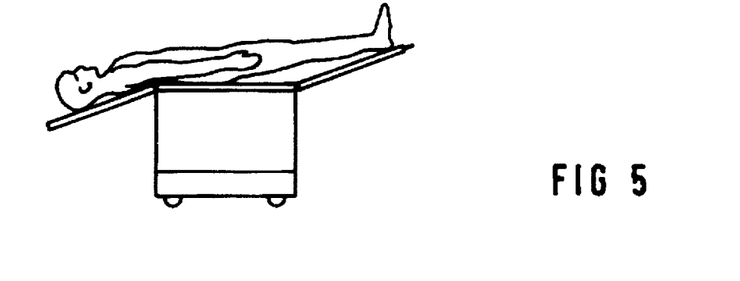
Figure 6:
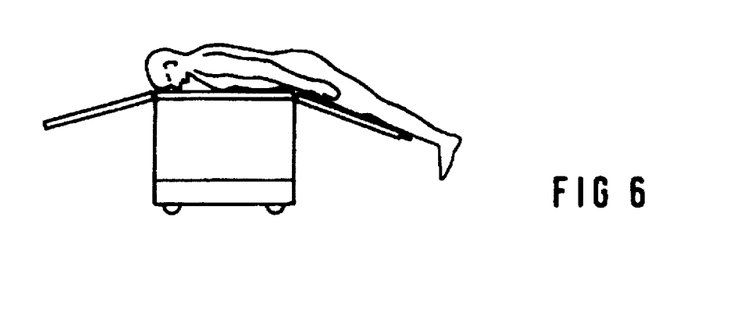
Figure 7:
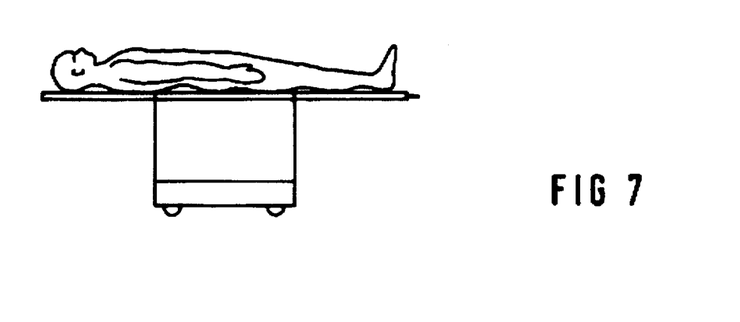

The upper part 6 and the bearing plate sections 12 and 13 have channels 14 through 17 along their edges, these channels 14 through 17 being provided for the acceptance of accessory parts, for example leg supports, infusion stands and the like. The possibility of being able to introduce accessory parts into the channels 14 through 17 is illustrated in FIG. 2, which shows an arm support 18 introduced into the channel 16 of the upper part 6.

As a result of the described adjustment possibilities of the articulated arm 4, the shockwave source 3 exhibits an adjustability that is adequate for reaching arbitrary points of at least the surface of the upper part 6 with the coupling membrane 19 provided for the application of the shockwave source 3 to a patient. In the described exemplary embodiment, however, the range of adjustment of the shockwave source 3 is so great that arbitrary locations of the patient bearing assembly formed by the upper part 6 and the bearing plate sections 12 and 13 can be reached with the coupling membrane 19.

Moreover, there is the possibility of also employing the therapy apparatus for treatment of a patient lying, for example, on an ordinary hospital bed or on a patient bearing unit other than the patient bearing assembly 6, 12 and 13 of the inventive therapy apparatus. To that end, the articulated arm 4 is pivoted in the direction of the double arrow β into the position indicated with broken lines in FIG. 1. The inventive therapy apparatus is also preferably brought into its space-saving standby position shown in FIG. 3, wherein the bearing plate sections 12 and 13 are pivoted down so as to press against the end faces of the base part 1.

In order to be able to push and maneuver the inventive therapy apparatus, moreover, gripping element or handle 20 is attached to the end face of the bearing plate section 13.

A swivel arm 21 having a platform 22 that is provided for the acceptance of the monitor 31 of the ultrasound apparatus 10 is provided at the column 5.

As shown in FIG. 9, the shockwave source 3 has a generally pot-shaped housing 23, a shockwave generator generally referenced 24 being provided in the region of one end thereof. At its open end, the housing 23 of the shockwave source 3 is closed with the flexible coupling membrane 19, with which the shockwave source 3 is pressed against the body of the patient P in a known way for acoustic coupling. The housing 23 is filled with water that is provided as acoustic propagation medium for the shockwaves emanating from the shockwave generator 24. The shockwave source 3 is in communication with the water supply 9 (see FIG. 8) via conduits that are not shown in FIG. 9. The shockwave source 3 is dynamically balanced relative to its central axis M.

The shockwave generator 24 is an electromagnetic shockwave generator. The shockwave generator 24 is preceded by an acoustic positive lens 25 that focusses the planar shockwaves emanating from the shockwave generator, which then converge in the focus zone F lying on the middle axis M as indicated with broken lines in FIG. 9. The shockwave generator 24 and the positive lens 25 are provided with respective central openings 26 and 27 aligned with one another, and through which a tube 28 extends in which the ultrasound applicator 29 of the ultrasound device 10 is arranged. This allows ultrasound B-images of a slice of the patient containing the middle axis M and the focus zone F to be produced.

The ultrasound locating system formed by the ultrasound applicator 29 and the ultrasound device 10 makes it possible to align the shockwave source 3 relative to the body of the patient in a known way such that a region to be charged with shockwaves, for example a painful shoulder or knee joint, is located in the focus zone F of the shockwaves. This occurs in a known way with the assistance of a mark F' identifying the focus zone F that is mixed into the ultrasound B-image displayed on a monitor 31 in a known way.

The ultrasound applicator 29, moreover, is longitudinally displaceable in the tube 28 in the direction of the middle axis M and is also arranged so as to be pivotable around the middle axis M in order to be able to generate an optimally undisturbed, informative ultrasound B-image dependent on the special circumstances of the treatment case, and in order to be able to bring the dome-shaped sound exit window of the ultrasound applicator 29 into engagement with that side of the coupling membrane 19 adjoining the acoustic propagation medium in the manner required for good image quality, while the other side thereof presses against the body surface of the patient. The position of the mark F' is thereby adapted in a known way to the respective position of the ultrasound applicator 29. The adjustment units required for the described adjustment of the ultrasound applicator 29 and the positional correction of the mark F' can be realized without difficulty by a person skilled in the art and are therefore not shown. As required, the ultrasound applicator 29 can be retracted during the generation of shockwaves to such an extent that it does not impede their propagation.

The shockwave generator 24 has a planar membrane containing electrically conductive material, for example copper or aluminum, having one side is adjacent to the water situated in the housing 23. On the other side of the membrane 32 a helically wound flat coil 34 is disposed that, for example, is attached to a coil carrier 35 by gluing. An insulating foil 33 is interposed between the flat coil 34 and the membrane 32. The flat coil 34 is in communication via terminals 36 and 37 with the high-voltage pulse generator 7, with which the flat coil 34 can be charged with high-voltage pulses having high amperage (kV and kA range). The high-voltage pulse generator 7 is fashioned in a known way so that the intensity of the shockwaves and the repetition rate of the shockwaves are adjustable. To this end, an operating panel 38 (FIG. 1) is provided at the platform 32 and is connected to the high-voltage pulse generator 7 to allow activation of the shockwave generator 24 as well as setting the aforementioned parameters.

When the flat coil 34 is charged with a high-voltage pulse, eddy currents that are directed oppositely to the current flowing through the flat coil 34 are induced in the membrane 32. This results in that the magnetic field associated with the eddy currents and the magnetic field associated with the current flowing through the flat coil 34 being oppositely directed. The membrane 32 thus moves suddenly away from the flat coil 34. A shockwave that is focussed with the acoustic positive lens 25 is therefore formed in the water located in the housing 23. The pulse duration of the generated shockwave lies in the μs range. The energy of the generated shockwave can lie on the order of magnitude of up to 120 millijoules, whereby the energy density in the focus can amount to up to approximately 0.6 millijoules/mm$^2$. The peak pressure in the focus can amount to up to 700 bar. Energy density and peak pressure can be arbitrarily reduced.

In order to facilitate preliminary examinations of patients, or in order to be able to employ the inventive therapy apparatus as an ultrasound diagnostic apparatus, there is the possibility of removing the ultrasound applicator 29 of the ultrasound device 10 from the shockwave source 3 and employing it independently thereof. When the ultrasound applicator 29 is removed, moreover, an appropriate plug (not shown) is introduced into the shockwave source in order to prevent the escape of water.

Although it is especially advantageous to employ an electromagnetic shockwave source of the type described since this type of source can be well-controlled, other shockwave sources can be employed within the scope of the invention, for example piezoelectric (U.S. Pat. No. 4,526,168), magnetostrictive, electrohydraulic (German OS 23 51 247) and other shockwave sources. Further, the pressure pulse source employed in the invention need not necessarily be a shockwave source.

Further, the radiation source need not necessarily be a pressure pulse source. Other acoustic radiation sources, for example ultrasound sources, can be employed.

Additionally, sources other than an acoustic radiation source can be employed, for example a source of electromagnetic radiation.

Although modifications and changes may be suggested by those skilled in the art, it is the intention of the inventor to embody within the patent warranted hereon all changes and modifications as reasonably and properly come within the scope of his contribution to the art.

I claim as my invention:

1. A therapy apparatus for use in a treatment room having a floor, comprising:
   a base part supportable on the floor of the treatment room;
   means for administering therapy including a radiation source mounted on said base part and a plurality of electrical components for operating said radiation source contained inside said base part;
   a patient support assembly; and
   an upper part attached to and covering said base part forming at least a part of said patient support assembly.

2. A therapy apparatus as claimed in claim 1 further comprising:

further parts and means for attaching said further parts to said base part, said further parts and said upper part forming, in combination, said patient support assembly.

3. A therapy apparatus as claimed in claim 2 wherein said means for attaching comprise means for temporarily attaching each of said further parts to said base part.

4. A therapy apparatus as claimed in claim 2 wherein said means for attaching comprise means for attaching at least one of said further parts to said base part at different locations on said base part.

5. A therapy apparatus as claimed in claim 2 wherein said means for attaching comprise means for permitting position adjustment of at least one of said further parts relative to said upper part.

6. A therapy apparatus as claimed in claim 1 further comprising means for mounting said radiation source to said base part for permitting adjustment of a position of said radiation source relative to said base part.

7. A therapy apparatus as claimed in claim 6 wherein said means for mounting comprises a column attached to and extending from said base part, and an articulated arm connecting said radiation source to said column.

8. A therapy apparatus as claimed in claim 6 wherein said means for mounting said radiation source comprise means for mounting said radiation source on said base part for permitting position adjustment of said radiation source in an adjustment range allowing arbitrary locations relative to said upper part to be attained by said radiation source.

9. A therapy apparatus as claimed in claim 6 wherein said means for mounting said radiation source comprise means for mounting said radiation source for permitting adjustment of a position of said radiation source in an adjustment range for reaching a patient disposed on said patient support assembly for administering therapy to said patient using said radiation source.

10. A therapy apparatus as claimed in claim 6 for use with a patient support unit, separate from said base part, and wherein said means for mounting said radiation source comprise means for mounting said radiation source on said base part for permitting position adjustment of said radiation source in an adjustment range allowing said radiation source to attain a position for administering therapy to a patient disposed on said separate patient support unit.

11. A therapy apparatus as claimed in claim 1 further comprising wheels at a bottom of said base part for permitting movement of said base part on said floor.

12. A therapy apparatus as claimed in claim 11 wherein one of said electrical components comprises means for storing energy sufficient for conducting at least one therapy procedure using said means for administering therapy.

13. A therapy apparatus as claimed in claim 12 wherein said means for storing energy comprise an electrical accumulator.

14. A therapy apparatus as claimed in claim 1 wherein said radiation source comprises a source of acoustic waves.

15. A therapy apparatus as claimed in claim 14 wherein said radiation source includes means for focussing said acoustic waves.

16. A therapy apparatus as claimed in claim 14 wherein said source of acoustic waves comprises a shockwave generator.

17. A therapy apparatus as claimed in claim 1 further comprising ultrasound locating means for locating a region of a patient to be treated by said radiation source.

18. A therapy apparatus as claimed in claim 17 wherein said ultrasound locating means includes a diagnostic ultrasound transducer, and wherein said diagnostic ultrasound transducer is disposed in said radiation source.

19. A therapy apparatus as claimed in claim 18 comprising means for removably mounting said diagnostic ultrasound transducer in said radiation source.

20. A therapy apparatus as claimed in claim 17 wherein said ultrasound locating means include a monitor for displaying an ultrasound image, and wherein said monitor is mounted on said base pad.

21. A therapy apparatus as claimed in claim 1 wherein said base part has a receptacle therein having an open top, in which said components are contained, and wherein said upper part comprises a cover closing said open top of said receptacle.

22. A therapy apparatus for use in a treatment room having a floor, comprising:

a base part supportable on the floor of the treatment room;

means for administering therapy including a radiation source mounted on said base part and a plurality of electrical components for operating said radiation source contained inside said base part;

a patient support assembly having a plane for supporting a patient; and an upper part attached to and covering said base part and forming at least said support plane of said patient support assembly.

* * * * *